(12) United States Patent
Hock et al.

(10) Patent No.: US 6,573,276 B2
(45) Date of Patent: Jun. 3, 2003

(54) MUSCARINIC M1 AGONIST AS AN INHIBITOR OF BETA-AMYLOID ($A\beta_{40}$ AND $A\beta_{42}$)-SYNTHESIS

(75) Inventors: Christoph Hock, Erlenbach (CH); Andreas Raschig, Biberach (DE); Marion Wienrich, Weiterstadt (DE); Roger Nitsch, Zollikon (CH); Klaus Mendla, Ingelheim (DE); Dieter Horst Meier, Marlow (GB); Klaus Bornemann, Ingelheim (DE); Cornelia Dorner-Ciossek, Ingelheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/135,808

(22) Filed: Apr. 30, 2002

(65) Prior Publication Data

US 2003/0050221 A1 Mar. 13, 2003

Related U.S. Application Data

(60) Provisional application No. 60/289,859, filed on May 9, 2001.

(51) Int. Cl.[7] ............................................. A61K 31/439
(52) U.S. Cl. ..................................................... 514/305
(58) Field of Search ......................................... 514/305

(56) References Cited

PUBLICATIONS

Emilien et al., Archives of Neurology, 57/4 (454–45) (2000)(abstract).*

* cited by examiner

*Primary Examiner*—Phyllis G. Spivack
(74) *Attorney, Agent, or Firm*—Robert P. Raymond; Timothy X. Witkowski; Mary-Ellen Devlin

(57) ABSTRACT

Methods of lowering the levels of $A\beta_{40}$, $A\beta_{42}$ and tau protein in a mammal comprising administering to the mammal an effective amount of talsaclidine, or a physiologically acceptable acid addition salt thereof, and methods of treating diseases associated with the formation of diffuse and senile plaques or $A\beta_{40}$-, $A\beta_{42}$- and tau-containing plaques are disclosed.

13 Claims, No Drawings

MUSCARINIC M1 AGONIST AS AN INHIBITOR OF BETA-AMYLOID ($A\beta_{40}$ AND $A\beta_{42}$)-SYNTHESIS The invention relates to the use of the functionally selective muscarinic M1 agonist talsaclidine for the preparation of a medicament for inhibiting β-amyloid synthesis and reduction in synthesis of tau proteins.

BACKGROUND OF THE INVENTION

Amyloid β-peptides (Aβ) are strongly aggregating peptides with approximate molecular masses of 4 kDa. The predominant forms, $A\beta_{40}$ and $A\beta_{42}$, are 40 and 42 amino acid residues in length, and are the major proteinaceous constituents of brain amyloid deposits in a variety of diseases. $A\beta_{42}$ is an early and central component of amyloid in diffuse and senile plaques, while $A\beta_{40}$ is the major peptide form in amyloid deposits in the cerebral microvasculature. $A\beta_{40}$ and $A\beta_{42}$ are derived by endoproteaolysis of the larger amyloid precursor protein (APP) by the combined activities of β-secretases that cleaves at the amino-terminus, and a γ-secretase that cleaves at the C-terminus, respectively, of the Aβ domain. Alternative amino-terminal cleavage by α-secretase within the Aβ domain results in the generation of non-amyloidogenic fragments. Because Aβ peptides readily aggregate into insoluble amyloid plaques, lowering their generation is a major objective for the design of therapeutic and preventive strategies for the treatment of a variety of diseases. Tau proteins are central to the neuropathology of, for instance, Alzheimer's disease and tau levels are increased in affected individuals.

BRIEF DESCRIPTIONS OF THE INVENTION

Surprisingly, it has been found that the selective muscarinic M1 agonist talsaclidine selectively decreases the cerebrospinal fluid (CSF) level of $A\beta_{42}$, $A\beta_{40}$, and tau protein; $A\beta_{40}$ and tau protein dose dependently. Accordingly, one embodiment of the current invention relates to the use of talsaclidine for the preparation of a medicament for lowering the level of $A\beta_{40}$, $A\beta_{42}$, and tau protein.

In a preferred embodiment the invention relates to the use of talsaclidine for the preparation of a medicament for the treatment or prophylaxis of diseases associated with the formation of diffuse and senile plaques.

Furthermore, the invention relates to the use of talsaclidine for the preparation of a medicament for the treatment or prophylaxis of diseases associated with the formation of $A\beta_{40}$-, $A\beta_{42}$-, and tau-containing plaques, preferably of $A\beta_{42}$-containing plaques.

Moreover, the invention relates to the use of talsaclidine for the preparation of a medicament for the treatment or prophylaxis of amyloidosis associated with the formation of $A\beta_{40}$, $A\beta_{42}$ and tau. Preferably the invention relates to the use of talsaclidine for the preparation of a medicament for the treatment or prophylaxis of amyloidosis associated with the formation of $A\beta_{42}$.

In particular, the invention relates to the use of talsaclidine for the preparation of a medicament for the treatment or prophylaxis of brain amyloidosis.

Furthermore, the invention relates to the use of talsaclidine for the preparation of a medicament for the treatment or prophylaxis of vascular amyloidosis and age-related amyloidosis.

Moreover, the invention relates to the use of talsaclidine for the preparation of a medicament for the treatment of patients suffering from mild to moderate dementia of Alzheimer-type (DAT). Patients suffering from mild to moderate dementia of Alzheimer-type show values of about 12–28, preferably 14–28 in the Mini Mental State Examination (MMSE).

Furthermore the invention relates to the use of talsaclidine for the preparation of a medicament for the prophylactic treatment of mild to moderate dementia of Alzheimer-type.

Moreover, the invention relates to the use of talsaclidine for the preparation of a medicament for the treatment of patients suffering from mild cognitive impairment (MCI) and mild age associated memory impairment (AAMI). Patients suffering from mild MCI and AAMI show values of about 23–28 in the Mini Mental State Examination (MMSE).

Furthermore the invention relates to the use of talsaclidine for the preparation of a medicament for the prophylactic treatment of mild cognitive impairment (MCI) and mild age associated memory impairment (AAMI).

DETAILED DESCRIPTION OF THE INVENTION

Talsaclidine 1 is described in U.S. Pat. No. 5,286,864, and possesses the following chemical structure

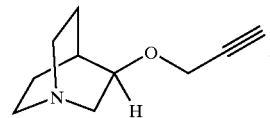

Talsaclidine is a functionally selective M1 agonist that stimulates α-secretase processing, and that lowers Aβ formation in cell culture and brain slice models. To test whether this effect also occurs in humans, talsaclidine or placebo were administered to 40 patients with clinical diagnosis of probable senile dementia of Alzheimer-type and measured cerebrospinal fluid (CSF) levels of $A\beta_{40}$ and $A\beta_{42}$ before and at the end of 4 weeks of treatment. To control for specificity, CSF levels of both total tau and phosphorylated tau were also measured. Surprisingly, it has been found that treatment with talsaclidine decreased CSF levels of $A\beta_{42}$, $A\beta_{40}$, and tau protein; $A\beta_{40}$ and tau protein dose dependently Accordingly, one embodiment of the current invention relates to the use of talsaclidine for the preparation of a medicament for lowering the levels of $A\beta_{40}$, $A\beta_{42}$, and tau protein. Preferably the invention relates to the use of talsaclidine for the preparation of a medicament for lowering the level of $A\beta_{42}$.

In a preferred embodiment of the invention relates to the use of talsaclidine for the preparation of a medicament for the treatment or prophylaxis of diseases associated with the formation of diffuse and senile plaques.

Furthermore, the invention relates to the use of talsaclidine for the preparation of a medicament for the treatment or prophylaxis of diseases associated with the formation of $A\beta_{40}$-, $A\beta_{42}$-, and tau-containing plaques. Preferably, the invention relates to the use of talsaclidine for the preparation of a medicament for the treatment or prophylaxis of diseases associated with the formation of $A\beta_{42}$-containing plaques.

Moreover the invention relates to the use of talsaclidine for the preparation of a medicament for the treatment or prophylaxis of amyloidosis associated with the formation of $A\beta_{40}$, $A\beta_{42}$ and tau. Preferably the invention relates to the use of talsaclidine for the preparation of a medicament for the treatment or prophylaxis of amyloidosis associated with the formation of $A\beta_{42}$.

In particular, the invention relates to the use of talsaclidine for the preparation of a medicament for the treatment or prophylaxis of brain amyloidosis.

Furthermore, the invention relates to the use of talsaclidine for the preparation of a medicament for the treatment or prophylaxis of vascular amyloidosis and age-related amyloidosis.

Moreover, the invention relates to the use of talsaclidine for the preparation of a medicament for the treatment of patients suffering from mild to moderate dementia of Alzheimer-type (DAT). Within the disclosure of the instant invention patients suffering from mild to moderate dementia of Alzheimer-type are characterized by values of about 12–28, preferably 14–28 in the Mini Mental State Examination (MMSE). MMSE is a methodology of grading the cognitive state of patients for the clinician well known in the art (J. Psychiat. Res., 1975, Vol 12., pp. 189–198).

Furthermore the invention relates to the use of talsaclidine for the preparation of a medicament for the prophylactic treatment of mild to moderate dementia of Alzheimer-type.

Moreover, the invention relates to the use of talsaclidine for the preparation of a medicament for the treatment of patients suffering from mild cognitive impairment (MCI) or age associated memory impairment (AAMI). Within the disclosure of the instant invention patients suffering from mild MCI or AAMI show values of about 23–28 in the Mini Mental State Examination (MMSE).

Furthermore the invention relates to the use of talsaclidine for the preparation of a medicament for the prophylactic treatment of mild cognitive impairment (MCI) or age associated memory impairment (AAMI).

Talsaclidine is preferably applied in form of its physiologically acceptable acid addition salts. According to the invention these physiologically acid addition salts are preferably selected from the salts formed by talsaclidine with hydrochloric acid, hydrobromic acid, sulfuric acid, phosphoric acid, methanesulfonic acid, acetic acid, fumaric acid, citric acid, tartaric acid, and maleic acid. Preferred salts are selected from the group consisting of hydrochloride, hydrobromide, sulfate, phosphate, fumarate, and methanesulfonate. More preferred salts are the hydrochloride, hydrobromide, and fumarate; talsaclidine fumarate being most preferred. Optionally the active ingredient is applied in form of a hydrate.

Methods

Diagnosis of probable Alzheimer's disease was made according to the National Institute of Neurological and Communicative Disorders and Stroke-Alzheimer's Disease and Related Disorders Association (NINCDS-ADRDA) as well as ICD10 criteria. All patients were community-dwelling and were referred to the participating dementia clinics from general practitioners, neurologists, and psychiatrists. All patients gave their informed consent and were screened for participation in a clinical phase II trial in accordance with GCP and ICH guidelines. The clinical phase II trial was designed to test the safety and tolerability of talsaclidine. CSF measurements were performed within a scientific add-on protocol and additional separate informed consent to the multicenter clinical trial.

Patients were carefully examined and received a thorough clinical work-up. Psychometric testing included the Mini Mental State Examination (MMSE) as a global screening instrument for dementia, the Alzheimer's Disease Assessment Scale, cognitive part (ADAScog), the Clinical Global Impression (CGI) and the Behavioral Pathology in AD (BEHAVE-AD). There were 40 participants in the study with two CSF samples each. Among the inclusion criteria were age below 85 years, MMSE between 12 and 28, and the absence of relevant systemic disorders.

Talsaclidine was given, in a randomized, double-blind design, three times per day (t.i.d) in a constant dosage with increasing dose panels. Both capsules or tablets of different dose strength were applied. The specific formulations used are outlined in detail below.

| Capsule 1 (2.5 mg Talsaclidine fumarate) | |
|---|---|
| Talsaclidine fumarate | 2.500 mg |
| Tablettose ® | 189.500 mg |
| Compritol ® (Glycerol behenate) | 8.000 mg |
| Hard gelatin | 80.000 mg |
| Total | 280.000 mg |

2.5 mg talsaclidine fumarate is equivalent to 1.47 mg talsaclidine.

| Capsule 2 (5 mg Talsaclidine fumarate) | |
|---|---|
| Talsaclidine fumarate | 5.000 mg |
| Tablettose ® | 187.000 mg |
| Compritol ® (Glycerol behenate) | 8.000 mg |
| Hard gelatin | 80.000 mg |
| Total | 280.000 mg |

5 mg talsaclidine fumarate is equivalent to 2.94 mg talsaclidine.

| Capsule 3 (20 mg Talsaclidine fumarate) | |
|---|---|
| Talsaclidine fumarate | 20.000 mg |
| Tablettose ® | 172.000 mg |
| Compritol ® (Glycerol behenate) | 8.000 mg |
| Hard gelatin | 80.000 mg |
| Total | 280.000 mg |

20 mg talsaclidine fumarate is equivalent to 11.76 mg talsaclidine.

| Capsule 4 (30 mg Talsaclidine fumarate) | |
|---|---|
| Talsaclidine fumarate | 30.000 mg |
| Tablettose ® | 162.000 mg |
| Compritol ® (Glycerol behenate) | 8.000 mg |
| Hard gelatin | 80.000 mg |
| Total | 280.000 mg |

30 mg talsaclidine fumarate is equivalent to 17.64 mg talsaclidine.

| Placebo (0 mg Talsaclidine fumarate) | |
|---|---|
| Talsaclidine fumarate | 0.000 mg |
| Tablettose ® | 192.000 mg |
| Compritol ® (Glycerol behenate) | 8.000 mg |
| Hard gelatin | 80.000 mg |
| Total | 280.000 mg |

| Tablet 1 (40.86 mg Talsaclidine fumarate) | |
|---|---|
| Core | |
| Talsaclidine fumarate | 40.86 mg |
| Lactose monohydrate (spray dried) | 173.34 mg |
| Microcrystalline cellulose | 102.00 mg |
| Sodium starch glycolate | 17.00 mg |
| Colloidal silicon dioxide | 3.40 mg |
| Stearic acid | 3.40 mg |
| Total (core) | 340.00 mg |
| Coating | |
| Hydroxypropylmethylcellulose | 1.1416 mg |
| Polyethyleneglycol 6000 | 1.4269 mg |
| Titanium dioxide | 1.5696 mg |
| Talcum | 4.5662 mg |
| Methacrylic acid copolymer (Eudragit) | 1.2843 mg |
| Total (coating) | 10.000 mg |
| Total (film tablet) | 350.000 mg |

-continued 40.86 mg talsaclidine fumarate is equivalent to 24 mg talsaclidine.
Tablet 2 (61.29 mg talsaclidine fumarate)

Core

| | |
|---|---|
| Talsaclidine fumarate | 61.29 mg |
| Lactose monohydrate (spray dried) | 152.91 mg |
| Microcrystalline cellulose | 102.00 mg |
| Sodium starch glycolate | 17.00 mg |
| Colloidal silicon dioxide | 3.40 mg |
| Stearic acid | 3.40 mg |
| Total (core) | 340.00 mg |

Coating

Same as Coating of Tablet 1

| | |
|---|---|
| Total (coating) | 10.000 mg |
| Total (film tablet) | 350.000 mg |

61.29 mg talsaclidine fumarate is equivalent to 36 mg talsaclidine.
Tablet 3 (81.72 mg Talsaclidine fumarate)

Core

| | |
|---|---|
| Talsaclidine fumarate | 81.72 mg |
| Lactose monohydrate (spray dried) | 132.48 mg |
| Microcrystalline cellulose | 102.00 mg |
| Sodium starch glycolate | 17.00 mg |
| Colloidal silicon dioxide | 3.40 mg |
| Stearic acid | 3.40 mg |
| Total (core) | 340.00 mg |

Coating

Same as Coating of Tablet 1

| | |
|---|---|
| Total (coating) | 10.000 mg |
| Total (film tablet) | 350.000 mg |

81.72 mg talsaclidine fumarate is equivalent to 48 mg talsaclidine.

The aforementioned capsules and tablets are obtainable using methods known in the art.

The aforementioned pharmaceutical compositions were administered twice daily or three times per day to the patients. The following dosings were applied: 4.5 mg talsaclidine (n=5 patients); 9 mg (n=4); 18 mg (n=4); 36 mg (n=4); 72 mg (n=4); 96 mg (n=4); 108 mg (n=4); 120 mg (n=2); 144 mg (n=3); and placebo (n=6). All capsules and tablets had an identical appearance to placebo and were administered in the same way.

Within one week of dementia testing and before treatment, CFS was obtained by lumbar puncture according to conventional techniques. CFS samples were frozen on dry ice immediately upon withdrawal at the bedside in 0.5 ml aliquots and stored at −85° C. until biochemical analyses. A second lumbar puncture was done after four weeks of treatment and the CFS obtained was processed identically to the initial lumbar puncture. All available CFS samples were included in the analyses.

A$\beta_{40}$ ELISA

Sandwich ELISA was performed with the capture antibody 6E10 (Senetek, Maryland Heights, Mo.). 6E10 is directed against the peptide sequence A$\beta$1–17. The detection antibody BAP-17 is specific for the free carboxyl terminus of A$\beta_{40}$. ELISA protocols were done as follows. Microplates (Nunc; Maxisorb) were coated with streptavidin (Roche Molecular Biochemicals) at 0.5 µl/ml concentration in carbonate buffer (100 mM sodium carbonate), followed by biotinylated 6E10 in blocking buffer (50 mM Tris-HCl pH 7.5; 140 mM NaCl; 5 mM EDTA; 0.05% NP40; 0.25% gelatin; 1% BSA). The samples were incubated for 24 hours followed by overnight incubation with the peroxidase-labeled detection antibody BAP17. Each assay plate included a standard curve with highly purified A$\beta_{40}$. After color development with 3,5,3',5'-tetramethylbenzidine (TMB) and hydrogen peroxide, absorbance was read at 450 nm on a microplate reader (Victor2 Multilabel, EG&G® Wallac). The linear range of the assay was 200 pg/ml to 20 ng/ml.

A$\beta_{42}$ ELISA

Sandwich ELISA was performed by using precoated plates (INNOTEST β-Amyloid 1–42, 8-well strips; Innogenetics, Belgium) with the capture antibody 21F12 (Innogenetics, Belgium). The capture 21F12 is specific for the free carboxyl terminus of A$\beta_{42}$ (peptide sequence A$\beta$33–42). After washing (5×, room temperature), biotinylated antibody 6E10 at 1 µl/ml concentration in blocking buffer (50 mM Tris-HCl pH 7.5; 140 mM NaCl; 5 mM EDTA; 0.05% NP40; 0.25% gelatine; 1% BSA) was added. Each assay plate included a standard curve with highly purified A$\beta_{42}$. After color development with TMP and Vectastain ABC detection (streptavidin-peroxidase complex, Vectastain Elite ABC Kit), absorbance was read at 450 nm. The linear range of the assay was 30 pg/ml to 5 ng/ml. There was no cross reactivity in either assay with A$\beta_{42}$ or A$\beta_{40}$.

Tau ELISA

The monoclonal antibody AT120 that reacts with both normal and HPF-tau was used in a sensitive sandwich ELISA (Innogenetics, Belgium). The detection limit was 10 pg/ml, the mean recovery 92%, the assay was linear in the range of 20 pg/ml to 1.2 ng/ml, and the intra-assay variance was below 11%. AT120-coated microtiter (Nunc, Maxisorb) were incubated with 25 µl unconcentrated CFS-samples. After washing with phosphate buffer, the non-phosphorylation dependent biotinylated monoclonal antibodies HT7 (epitope: aa 159–163) and BT2 (epitope: aa 194–198) were used as capturing reagents. After incubation with peroxidase-conjugated streptavidin and a final washing, TMB was added as chromogen. Absorbance was read at 450 nm.

Phosphotau ELISA

The monoclonal antibody AT270 that specifically with tau proteins phosphorylated at threonine 181 was used in a sensitive sandwich ELISA (Innogenetics, Belgium). The detection limit was 3 pg/ml, the mean recovery 100%, the assay was linear in the range 8 to 80 pm/ml. AT270-precoated microtiter plates were incubated with 25 µl unconcentrated CSF-samples. After washing, the biotinylated monoclonal antibody HT7 was used as capturing reagent. After incubation with peroxidase-conjugated streptavidin and a final washing, TMB was added as chromogen. Absorbance was read at 450 nm.

Statistical Analyses

Statistical analyses of data were done by Wilcoxon signed-rank tests for paired samples as well as by the Mann-Whitney U test for group comparisons. Bonferroni correction for multiple testing was performed. Analyses of covariates were used to test whether changes correlated with age, gender, or dementia severity.

Results

CSF levels of A$\beta_{42}$ at baseline ranged from 0.010 to 0.487 ng/ml (n=40). Mean A$\beta_{42}$ concentrations were 0.118±0.125 ng/ml (mean±SD). After four weeks of treatment with talsaclidine, the mean CSF levels of A$\beta_{42}$ decreased from 0.126±0.073 ng/ml (n-34). No change in CSF levels of A$\beta_{42}$ was observed during treatment with placebo (0.072±0.059 to 0.071±0.060 ng/ml, n=6). Treatment with talsaclidine decreased CSF levels of A$\beta_{42}$ significantly over time within the treatment group (n=34) by a median of 17% as well as compared to placebo (n=6) by a median of 23%, however not dose dependently. CSF levels of $A\beta_{42}$ decreased in 65% of the patients treated with talsaclidine, 15% did not change, and 20% increased. The largest percent decreases in CSF levels of $A\beta_{42}$ from baseline during treatment with talsaclidine occurred in patients with high CSF levels of $A\beta_{42}$ at baseline as demonstrated by regression analysis.

CSF levels of $A\beta_{40}$ did not increase in total in comparison to placebo, but decreased dose dependently. Tau (n=34) again did not decrease in total in comparison to placebo, but decreased dose dependently.

We claim:

1. A method of lowering the levels of $A\beta_{40}$, $A\beta_{42}$, and tau protein in a mammal comprising administering to the mammal an effective amount of talsaclidine or a physiologically acceptable acid addition salt thereof.

2. The method according to claim 1, wherein the mammal is a human.

3. A method of lowering the level of at least one of $A\beta_{40}$, $A\beta_{42}$, or tau protein in a mammal comprising administering to the mammal an effective amount of talsaclidine or a physiologically acceptable acid addition salt thereof.

4. The method according to claim 3, wherein the mammal is a human.

5. A method for the treatment of a disease associated with the formation of $A\beta_{40}$-, $A\beta_{42}$- and tau-containing plaques the method comprising administering to a mammal in need of such treatment an effective amount of talsaclidine or a physiologically acceptable acid addition salt thereof.

6. The method according to claim 5, wherein the disease is amyloidosis.

7. The method according to claim 6, wherein the disease is brain amyloidosis.

8. The method according to claim 6, wherein the disease is vascular amyloidosis.

9. The method according to claim 6, wherein the disease is age-related amyloidosis.

10. The method according to claim 5, wherein the disease is mild to moderate dementia of Alzheimer type (DAT).

11. The method according to claim 5, wherein the disease is mild cognitive impairment (MCI).

12. The method according to claim 5, wherein the disease is age associated memory impairment (AAMI).

13. The method according to claim 5, wherein the mammal is a human.

* * * * *